United States Patent
Shaik et al.

(10) Patent No.: US 12,406,368 B2
(45) Date of Patent: Sep. 2, 2025

(54) VISUAL ANALYSIS OF SPERM DNA FRAGMENTATION

(71) Applicant: VitruvianMD PTE Ltd, Singapore (SG)

(72) Inventors: Ifthakaar Shaik, Sandton (ZA); Pu-Ju Lin, Woodmead Ext. (CA); Byron Alexander Jacobs, Johannesburg (CA)

(73) Assignee: VitruvianMD PTE Ltd, Singapore (SG)

( * ) Notice: Subject to any disclaimer, the term of this patent is extended or adjusted under 35 U.S.C. 154(b) by 0 days.

(21) Appl. No.: 19/084,122

(22) Filed: Mar. 19, 2025

(65) Prior Publication Data
US 2025/0238927 A1    Jul. 24, 2025

Related U.S. Application Data

(63) Continuation of application No. PCT/IB2023/059595, filed on Sep. 27, 2023.

(30) Foreign Application Priority Data

Oct. 17, 2022   (ZA) .................................. 2022/11329

(51) Int. Cl.
*G06T 7/00*       (2017.01)
*G16B 40/00*   (2019.01)

(52) U.S. Cl.
CPC ............ *G06T 7/0012* (2013.01); *G16B 40/00* (2019.02); *G06T 2207/10016* (2013.01);
(Continued)

(58) Field of Classification Search
CPC ......... G06T 2207/10056; G06T 7/0012; G06T 2207/30004; G06T 2207/30024; G06T 2207/20036
See application file for complete search history.

(56) References Cited

U.S. PATENT DOCUMENTS

| 2008/0138816 A1 | 6/2008 | Brawley et al. |
| 2015/0031019 A1 | 1/2015 | Nordbo et al. |
| 2021/0209524 A1 | 7/2021 | Oppelstrup et al. |

FOREIGN PATENT DOCUMENTS

| JP | 2012198249 A | 10/2012 |
| WO | WO 2016178234 A1 | 11/2016 |

(Continued)

OTHER PUBLICATIONS

McCallum, Christopher, et al. "Deep learning-based selection of human sperm with high DNA integrity." Communications biology 2.1 (2019): 250. (Year: 2019).*

(Continued)

*Primary Examiner* — Raphael Schwartz
(74) *Attorney, Agent, or Firm* — Fish & Richardson P.C.

(57) ABSTRACT

The present invention relates to a method for analysing DNA fragmentation in a sperm cell by approximating the output of a pre-selected chemical assay of sperm DNA fragmentation. According to a first aspect of the present invention, there is provided a method for analysing DNA fragmentation in a sperm cell by approximating the output of a pre-selected chemical assay of sperm DNA fragmentation, the method comprising:
  providing an image of the sperm cell, under brightfield and/or phase contrast with a total magnification of 400× to 1000×;
  evaluating the image of the sperm cell to identify and/or measure a pre-selected biomarker; and
  approximating the output of the pre-selected chemical assay of sperm DNA fragmentation of the sperm cell by subjecting the identified and/or measured biomarker to a first machine learning analysis.

18 Claims, 2 Drawing Sheets

Figure 1:
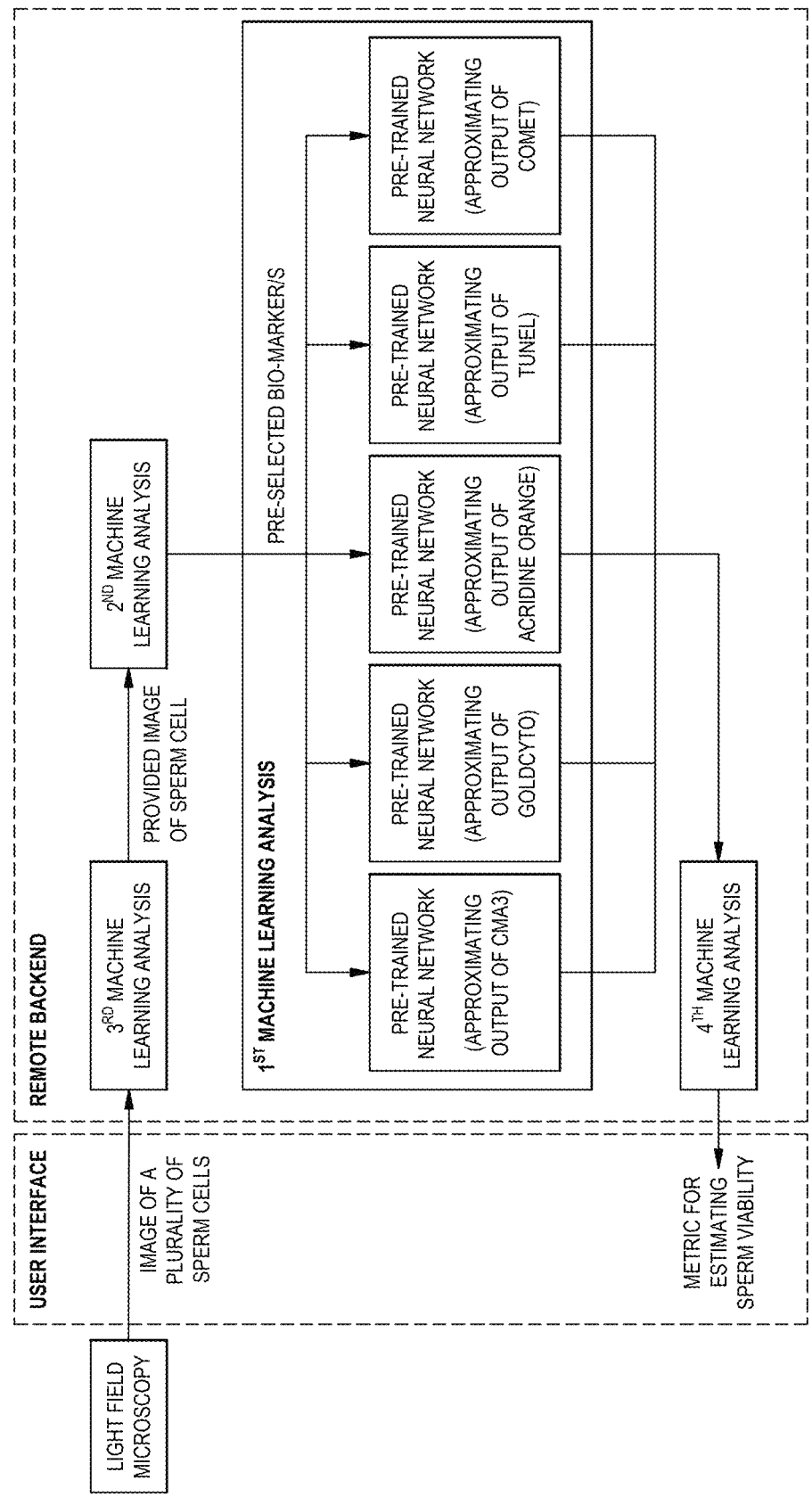

(52) U.S. Cl.
CPC .............. *G06T 2207/10056* (2013.01); *G06T 2207/20016* (2013.01); *G06T 2207/20036* (2013.01); *G06T 2207/20081* (2013.01); *G06T 2207/20084* (2013.01); *G06T 2207/30024* (2013.01); *G06T 2207/30204* (2013.01)

(56) References Cited

FOREIGN PATENT DOCUMENTS

| | | |
|---|---|---|
| WO | WO 2019150365 A1 | 8/2019 |
| WO | WO 2021200003 A1 | 10/2021 |
| WO | WO 2021259903 A1 | 12/2021 |

OTHER PUBLICATIONS

Wang, Yihe, et al. "Prediction of DNA integrity from morphological parameters using a single-sperm DNA fragmentation index assay." Advanced Science 6.15 (2019): 1900712. (Year: 2019).*

Yüzkat, Mecit, Hamza Osman Ilhan, and Nizamettin Aydin. "Multi-model CNN fusion for sperm morphology analysis." Computers in biology and medicine 137 (2021): 104790. (Year: 2021).*

Agarwal et al., "The Society for Translational Medicine: clinical practice guidelines for sperm DNA fragmentation testing in male infertility," Translational Andrology and Urology, Sep. 2017, 6(Suppl 4):S720-S733.

Dimitriadis et al., "Automated smartphone-based system for measuring sperm viability, DNA fragmentation, and hyaluronic binding assay score," PLoS One, Mar. 13, 2019, 14(3):e0212562, 12 pages.

Eggert-Kruse et al., "The Acridine Orange test: a clinically relevant screening method for sperm quality during infertility investigation?," Human Reproduction, Apr. 1, 1996, 11(4):784-9.

Ghasemzadeh et al., "Sperm parameters, protamine deficiency, and apoptosis in total globozoospermia," Iranian Journal of Reproductive Medicine, Aug. 2015, 13(8):495-502.

Hosseinifar et al., "Correlation between sperm DNA fragmentation index and CMA3 positive spermatozoa in globozoospermic patients," Andrology, May 2015, 3(3):526-31.

International Preliminary Report on Patentability in International Appln. No. PCT/IB2023/059595, mailed on Sep. 4, 2024, 11 pages.

International Search Report and Written Opinion in International Appln. No. PCT/IB2023/059595, mailed on Feb. 7, 2024, 9 pages.

Martins et al., "The use of the acridine orange test and the TUNEL assay to assess the integrity of freeze-dried bovine spermatozoa DNA," Genetics and Molecular Research, Mar. 15, 2007, 6(1):94-104.

Mateo-Otero et al., "Sperm DNA damage compromises embryo development, but not oocyte fertilisation in pigs," Biological Research, Apr. 1, 2022, 55(1):15, 12 pages.

Pérez-Cerezales et al., "Comparison of four methods to evaluate sperm DNA integrity between mouse caput and cauda epididymidis," Asian Journal of Andrology, Oct. 17, 2011, 14(2):335-337.

Ribas-Maynou et al., "Sperm DNA integrity does play a crucial role for embryo development after ICSI, notably when good-quality oocytes from young donors are used," Biological Research, Dec. 26, 2022, 55(1):41, 14 pages.

Santi et al., "Sperm DNA fragmentation index as a promising predictive tool for male infertility diagnosis and treatment management—meta-analyses," Reproductive Biomedicine Online, Sep. 1, 2018, 37(3):315-26.

Sedó et al., "Effect of sperm DNA fragmentation on embryo development: clinical and biological aspects," JBRA Assisted Reproduction, Oct. 2017, 21(4):343-350.

Serrano Berenguer et al., "Abstract #: P-101: Machine and deep learning models to classify comet assay tests for sperm DNA fragmentation evaluation," Abstract, Presented at 38th Hybrid Annual Meeting of the ESHRE, Milan, Italy, Jul. 3-6, 2022; Human Reproduction, Jul. 1, 2022, 37(Supplement_1):i237.

Shamsi et al., "Sperm DNA integrity assays: diagnostic and prognostic challenges and implications in management of infertility," Journal of Assisted Reproduction and Genetics, Nov. 2011, 28:1073-85.

Shibahara et al., "Clinical significance of the Acridine Orange test performed as a routine examination: comparison with the CASA estimates and strict criteria," International Journal of Andrology, Aug. 2003, 26(4):236-41.

SuperComputer's Blog [online], "Understanding Bilinear Image Resizing" Jul. 19, 2018, retrieved on Mar. 28, 2025, retrieved from URL <https://chao-ji.github.io/jekyll/update/2018/07/19/BilinearResize.html>, 10 pages.

Wang et al., "Prediction of DNA integrity from morphological parameters using a single-sperm DNA fragmentation index assay," Advanced Science, Aug. 2019, 6(15):1900712, 10 pages.

\* cited by examiner

VISUAL ANALYSIS OF SPERM DNA FRAGMENTATION

CROSS-REFERENCE TO RELATED APPLICATIONS

This application is a continuation of International Application No. PCT/IB2023/059595, having an International Filing Date of Sep. 27, 2023, which claims priority to South Africa Application No. 2022/11329, filed on Oct. 17, 2022, the disclosures of both of which are considered part of the disclosure of this application, and are incorporated by reference in its entirety into this application.

FIELD OF APPLICATION OF THE INVENTION

The present invention relates to a method for analysing DNA fragmentation in a sperm cell by approximating the output of a pre-selected chemical assay of sperm DNA fragmentation.

BACKGROUND TO THE INVENTION

The analysis, diagnosis and selection of spermatozoa (sperm) is of high importance in the field of reproductive health. Here, sperm quality may be assessed along a number of axes. Morphological assessments and assessments of sperm DNA fragmentation are two of these axes. In terms of assessments of sperm DNA fragmentation, these are presently done using chemical assays. A number of such assays are known in the art, including the Chromomycin A3 (CMA3) assay, Acridine Orange (AO) assay, Sperm Chromatin Structure Assay (SCSA), GoldCyto assay, various sperm chromatin dispersion (SCD) tests, Terminal deoxynucleotidyl transferase dUTP Nick End-Labelling (TUNEL) assay, Toluidine Blue, Aniline Blue and Single Cell Gel Electrophoresis (COMET assay). The prime disadvantage of such assays is that they inactivate the sperm being studied—rendering it unusable for reproductive health interventions such as in vitro fertilization (IVF) or intracytoplasmic sperm injection (ICSI). This also results in significant amounts of medical waste being generated, which includes the chemicals used in the assays. Additionally; some assays are limited to qualitative or binary outcomes (fragmented vs non-fragmented) rather than quantitative outcomes. Fragmentation assays may also not be directly correlated with viability.

US Patent No. 2015/031019 discloses a method for identifying and selecting high motility, normal morphology and high DNA integrity spermatozoa comprising: (a) receiving a sperm sample; (b) determining one or more characteristics of each spermatozoon in the sperm sample; and (c) determining a sperm kinetic profile of the spermatozoon in the sperm sample; (d) and associating the sperm kinetic profile with an index set, wherein the index includes information indicative of an identity of the sperm kinetic profile. This patent accordingly discloses a non-chemical method for visually identifying and selecting sperm cells based on DNA integrity.

PCT Patent application No. WO 2019/150365 discloses a method for evaluating fertility potential of a living sperm cell, the method comprising: providing a predetermined classification function correlating between one or more physio spatial parameters of sperm cells and DNA fragmentation distribution in sperm cells; providing data indicative of said one or more physio spatial parameters of the living sperm cell; and applying said classification function to said one or more physio spatial parameters of the living sperm cell to thereby determine a DNA fragmentation level, inside said DNA fragmentation distribution, in said living sperm cell, the DNA fragmentation level being indicative of the fertility potential of the living sperm cell. Here, the step of providing data indicative of said one or more physio spatial parameters of the living sperm cell is further disclosed as comprising measurement of said living sperm cell with quantitative phase microscopy.

PCT Patent application No. WO 2021/200003 discloses an imaging processing apparatus, making use of a microscope, that acquires captured images of a sample containing sperm placed on the stage of the microscope. Based on the captured images, an auxiliary image including auxiliary information that contributes to sperm selection is generated. The apparatus further includes an image processing device for superimposing the auxiliary image generated by the image processing device onto an optical image of the sample formed on an image plane on the optical path of the microscope. The image processing apparatus includes object detection for sperm for the captured image and recommendation degree estimation for estimating the "recommendation degree" of sperm detected by the object detection. The use of a sperm DNA Fragmentation Index (DFI) is further disclosed in combination with the apparatus.

JP Patent No. 2012-198249 discloses a method for measuring sperm head vacuoles, comprising: (a) a step of measuring the number and width of vacuoles in the sperm head; (b) a width (C) of the vacuoles and a sperm head width (D). The vacuoles are then classified according to the value of C/D as follows: (I) A vacuole with a C/D value greater than ½ (vacuum L) has a score of 3, and (II) a C/D value of 1 Vacuole (vacuum M) of/3 or larger and ½ or smaller has a score of 2, (III) vacuole (vacuum S) of C/D smaller than ⅓ has a score of 1, and (IV) a step of classifying and scoring according to a score of 0 if there is no vacuole. There is additionally a step (c) which comprises calculating a sperm head vacuole area score by using a formula. The patent further discloses the use of a DNA fragmentation index in combination with the disclosed method.

PCT Patent application No. WO 2016/178234 discloses a method for use in sperm analysis, the method comprising processing measured data comprising at least interferometric phase data of a label-free sperm cell, said processing of the measured data comprising determining topographic optical phase delay (OPD) map of the label-free sperm cell, determining at least one physical parameter of the label-free sperm cell, and generating data indicative of sperm quality for the label-free sperm cell. The patent application further discloses a training data set comprising spatial, spectral and polarization state and birefringence distribution within a sperm cell, that such a data set is indicative of sperm quality, and that sperm quality is indicative of at least one of chromosomal aberrations within a nucleus of the cell, DNA fragmentation within the cell and sex of the sperm cell.

Dimitriadis et al (Dimitriadis, I., L. Bormann, C., Kanakasabapathy, M. K., Thirumalaraju, P., Kandula, H., Yogesh, V., Gudipati, N., Natarajan, V., C. Petrozza, J., & Shafiee, H. (2019); Automated smartphone-based system for measuring sperm viability, DNA fragmentation, and hyaluronic binding assay score. PLOS ONE, 14(3), e0212562) discloses a system making use of a smartphone-based system for laboratory use in measuring: a) Hyaluronan Binding Assay (HBA) score, a quantitative score describing the sperm maturity and fertilization potential in a semen sample, b) sperm viability, which assesses sperm membrane integrity, and c) sperm DNA fragmentation that assesses the degree of DNA damage. Here the authors found that there was good correlation between the manual analysis and smartphone-based analysis for the HBA, with the smartphone-based approach performing with an accuracy of 87% in sperm classification when the HBA score was set at manufacturer's threshold of 80. Similarly, the sperm viability and DNA fragmentation tests were also shown to be compatible with the smartphone-based system.

In view of the above, there is accordingly a clear need for a method of assaying sperm quality, along a number of different axes, which replicates the results obtained by pre-existing chemical assays and which may additionally provide a quantitative measure of viability. The assay should also ideally be non-destructive and applicable to use with live sperm. Finally; such an assay should ideally make use of commonly-available equipment and methodologies (such as conventional light microscopy), and should not use toxic or exotic reagents.

OBJECT OF THE INVENTION

Accordingly, it is an object of the present invention to provide a method for analysing DNA fragmentation in a sperm cell, with which the Applicant believes the aforementioned disadvantages may at least be alleviated or which may provide a useful alternative for the known art.

It is a further object of the present invention to provide a method for estimating sperm viability.

SUMMARY OF THE INVENTION

According to a first aspect of the present invention, there is provided a method for analysing DNA fragmentation in a sperm cell by approximating the output of a pre-selected chemical assay of sperm DNA fragmentation, the method comprising:
   providing an image of the sperm cell, under brightfield and/or phase contrast with a total magnification of 400× to 1000×;
   evaluating the image of the sperm cell to identify and/or measure a pre-selected biomarker; and
   approximating the output of the pre-selected chemical assay of sperm DNA fragmentation of the sperm cell by subjecting the identified and/or measured biomarker to a first machine learning analysis.

In an embodiment of the invention, the step of evaluating the image of the sperm cell is carried out using a second machine learning analysis. In a preferred embodiment, the second machine learning analysis may be carried out using a pre-trained neural network. In a preferred embodiment, the pre-trained neural network used to perform the step of evaluating the image of the sperm cell may be trained using image data comprising brightfield and/or phase contrast images of sperm cells at a total magnification of 400× to 1000×.

In an embodiment of the invention, the pre-trained neural network may be a classification network.

The invention provides for the pre-trained neural network to use a deep convolutional neural network architecture.

In an embodiment of the invention, the pre-trained neural network may be trained with a binary cross entropy loss function or mean squared error loss function.

In an embodiment, the pre-trained neural network may include a final layer having a node appended with sigmoidal activation.

The pre-trained neural network may include layers selected from the group consisting of a dense layer, a batch normalisation layer, a Rectified Linear Unit (ReLU) layer, a prediction layer and a dropout layer, in any combination.

Here, it should be understood that reference to a pre-trained neural network, both in regards to the above-mentioned and any subsequently mentioned pre-trained neural networks referred to herein below, may include many variations on neural network architectures, topologies, training methods and loss functions as known in the art.

In an embodiment, the first machine learning analysis may be carried out using a pre-trained neural network. In a preferred embodiment, the pre-trained neural network used to carry out the first machine learning analysis may be trained using image data comprising brightfield, phase contrast or fluorescent images of sperm cells, before and after staining with the pre-selected chemical assay.

It should be understood that the first machine learning analysis can be applied to either a single pre-selected assay, or to a plurality thereof.

Where the first machine learning analysis is carried out with a pre-trained neural network, then such an analysis may be performed using either individual pre-trained neural networks, or a single network, or a core network having one or more activatable layers to accommodate each pre-selected chemical assay, or a combination thereof, as is well known in the art.

The pre-trained neural network may also form a component of the pre-trained neural network used to perform the step of evaluating the image of the sperm cell, as well as any subsequent preferred embodiments making use of a pre-trained neural network.

Alternatively; the outputs of one or more pre-trained neural networks used in any of the steps of the method for analysing DNA fragmentation in a sperm cell by approximating the output of a pre-selected chemical assay of sperm DNA fragmentation may be used as inputs for other pre-trained neural networks used in any of the other steps.

In an embodiment of the invention, the step of providing an image may further comprise:
   providing an image of a plurality of sperm cells; and
   isolating the image of the sperm cell from the image of a plurality of sperm cells.

In a preferred embodiment, the step of isolating an image of the sperm cell may be carried out using a third machine learning analysis.

In a preferred embodiment, the third machine learning analysis is carried out using a third pre-trained neural network.

In another alternative preferred embodiment, the step of providing an image may yet further comprise a step of rescaling the image of the sperm cell to approximate an image captured at a different magnification. In a preferred embodiment, the image of the sperm cell may be rescaled using bilinear interpolation. In an alternative preferred embodiment, the image of the sperm cell may be rescaled to approximate an image captured at a magnification of 1000×.

The method may further comprise a final step of synthesis of the output of the first and/or second machine learning analysis into a metric for estimating sperm viability.

In a preferred embodiment, the synthesis may be carried out using a fourth machine learning analysis. In a further preferred embodiment, the fourth machine learning analysis may be carried out using a fourth pre-trained neural network.

In an embodiment, the sperm cell may be a live sperm cell.

The pre-selected biomarker may be selected from the group consisting of area, perimeter, width, length, eccentricity/ellipticity, roughness, elongation and regularity.

Here, it should be understood that such metrics may be expressed with regard to either the whole sperm cell, or a sub-component thereof, a ratio of the whole cell to a sub-component, a ratio of one sub-component to another sub-component, or a mathematical equation wherein one or more of the metrics related to the whole sperm cell and/or one or more subcomponents thereof are used as variables in the equation.

In an embodiment of the invention, the output of the pre-selected chemical assay of sperm DNA fragmentation may be selected from the group consisting of DNA Fragmentation Index (DFI) and measure of DNA fragmentation. Here the term "DNA Fragmentation Index" is a known term in the art, and relates to the output of the Acridine Orange (AO) chemical assay. Similarly, "measure of DNA fragmentation" relates to a known term in the art used to describe the output of other, qualitative chemical assays such as GoldCyto and Chromomycin A3 (CMA3). Accordingly; approximating the output of such qualitative assays should be understood to include the results of known methods and approaches in the art for assessing such a qualitative assay. For instance, and by way of a non-limiting example, such a method of assessment may include the establishing of a quantitative, pre-selected threshold relating to the measured output value and selected with reference to clinical practice. A variety of such methods and approaches, as known in the art, may accordingly be envisaged here.

The pre-selected chemical assay may be selected from the group consisting of Chromomycin A3 (CMA3), Acridine Orange (AO), Sperm Chromatin Structure Assay (SCSA), GoldCyto, sperm chromatin dispersion (SCD) test, and Terminal deoxynucleotidyl transferase dUTP Nick End-Labelling (TUNEL) assay, Aniline Blue, Toluidine Blue and COMET.

In an embodiment, the image may be a plurality of images. In a preferred embodiment, the plurality of images may be in the form of a video.

The image may be a microscope image. In a preferred embodiment, the microscope image may be at a magnification of between 250× and 1500×. In a further preferred embodiment, the magnification may be 400×. In an alternative embodiment, the magnification may be 1000×.

The above and other characteristics, features and advantages of the present invention will become apparent from the following detailed description, taken in conjunction with the accompanying drawings which illustrates, by way of example, the principles of the invention. This description is given for the sake of example only, without limiting the scope of the invention. The reference figures quoted below refer to the attached drawings.

BRIEF DESCRIPTION OF THE ACCOMPANYING DIAGRAMS

Figure 2:
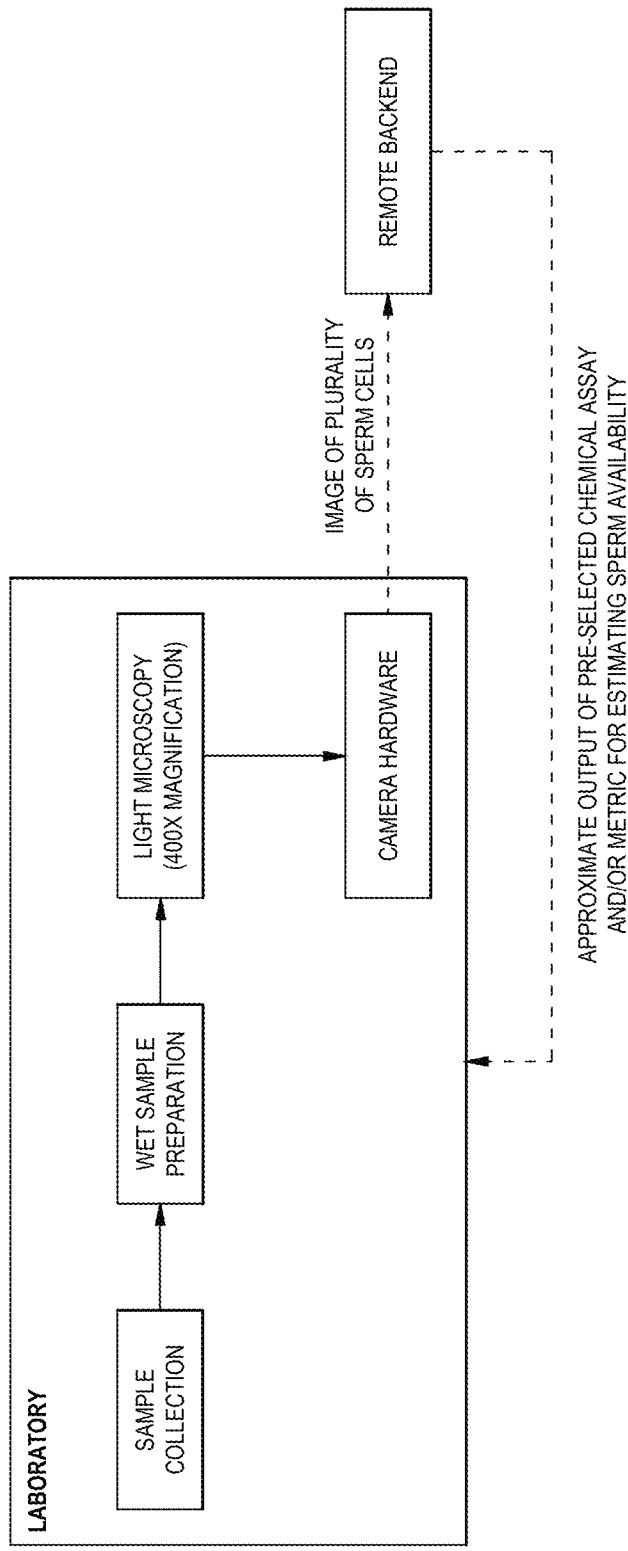

The invention will now further be described, by way of example only, with reference to the accompanying diagrams wherein:

FIG. 1 is a schematic representation of a preferred embodiment of the method of the invention; and FIG. 2 is a schematic representation of a use case scenario wherein live sperm samples are collected, processed, imaged and then forwarded to a remote backend implementing a preferred embodiment of the method of the invention.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

DESCRIPTION OF EXAMPLE EMBODIMENTS OF THE INVENTION

In a non-limiting example embodiment, and with reference to FIGS. 1 and 2 of the invention, the method of the invention is applied to dynamic sperm analysis from video data, for use as a clinical sperm selection tool for in vitro fertilization (IVF) or intracytoplasmic sperm injection (ICSI).

Here the following wet sample preparation method is performed prior to a method of analysis, with the entire semen volume being used. For this preparation method, it should be noted that a maximum of 1.5 ml of semen should be used when processing with purer sperm gradients. If the total semen volume exceeds 1.5 ml, then parallel processing must be done.

The preparation is done according to the following steps, which are taken from the WHO laboratory manual for the examination and processing of human semen (W. H. Organization, et al., WHO laboratory manual for the examination and processing of human semen (2010)):

i) Layer the gradients and semen immediately after liquefaction and check pre-counts while the sample is spinning.
ii) Layer 2 ml of 80% density gradient first.
iii) Layer 2 ml of 40% density gradient on top of 80% layer.
iv) Layer semen (max 1.5 ml) on top of 40% layer.
v) Centrifuge for 20 min at 2000G.
vi) Prepare a disposable pipette before the end of the first spin to remove the top layers of media. When removing the supernatant, be careful not to disturb the sperm pellet.
vii) Remove the pellet with a 100-1000 µl pipette to prevent excess debris from being transferred to the wash media.
viii) Place only the tip of the pipette into the wash media.
ix) Add the pellet slowly allowing the sample to mix. Note, do not tip the test tube to mix the sample, rather run the test tube over your fingers a few times.
x) Spin the sample for the second time for 10 min at 1500G. Prepare a disposable pipette.
xi) When the second spin is complete, remove the supernatant in the same fashion as the first time.
xii) 20 µl is then pipetted onto a slide and cover slip is placed over sample.
xiii) The slide is then ready to be assessed.

Following the slide preparation, a preferred example embodiment of the method for analysing DNA fragmentation in a sperm cell by approximating the output of a pre-selected chemical assay of sperm DNA fragmentation is conducted. Here, the first step of providing an image of the sperm cell is carried out under a microscope using either brightfield or phase contrast imaging with a 40× objective lens at 400× magnification. The images are captured using a digital camera (VisionMD camera hardware and online software capturing suite) as a plurality of images in the form of video, each frame of which comprises an image of a plurality of sperm cells. These images are then electronically forwarded to a remote backend wherein the method of the invention is carried out.

At the remote backend, isolation of an image of the sperm cell from the plurality of sperm cells is carried out using machine learning analysis, which in turn is carried out using a pre-trained neural network. The neural network isolates the image of the sperm cell from the image of a plurality of sperm cells. Following isolation, the image of the sperm cell is rescaled to approximate an image captured at 1000× magnification using bilinear interpolation.

Following image isolation and rescaling, the image of the sperm cell is evaluated to identify a number of pre-selected biomarkers using machine learning analysis, which is carried out using a pre-trained neural network trained using image data comprising brightfield images of sperm cells. These biomarkers comprise the following:

Area: the total area (measured in $\mu m^2$) of the detected spermatozoa head region (excluding the neck and tail);
Perimeter: the perimeter (measured in $\mu m$) of the detected spermatozoa head region only;
Width (w): the width (measured in $\mu m$) of the detected spermatozoa head along the minor axis;
Length (l): the width (measured in $\mu m$) of the detected spermatozoa head along the major axis;
Eccentricity/Ellipticity: eccentricity and ellipticity are both measures of how circular the sperm head is. An eccentricity (or ellipticity) of 0 corresponds to a perfectly circular sperm head. Morphologically normal sperm should have an elliptic head shape, and hence an eccentricity (or ellipticity) >0;
Roughness: roughness measures how significantly the perimeter of the observed shape deviates from the smoothest shape of the same area. For example, a circle has a roughness of 1. Roughness is measured here in terms of $(4\pi*Area)/(Perimeter^2)$;
Elongation: elongation measures the proportion of the difference in width and length to the sum of width and length, measured here in terms of $(w-l)/(w+l)$. Elongation is 0 if the major axis and minor axis are equal, and is maximally 1; and
Regularity: a measure of the observed spermatozoon's regularity. Specifically, the scaled ratio of the rectangular area in which the spermatozoon is embedded to the observed area. Regularity is measured here in terms of $(l*w*\pi)/(4*Area)$.

The pre-selected biomarkers, once evaluated, are used as inputs for machine-learning analysis, carried out using a pre-trained neural network trained using image data comprising brightfield and/or phase contrast images of sperm cells or fluorescent images of sperm cells, before and after staining with the pre-selected chemical assay, to approximate the output of the pre-selected chemical assay of sperm DNA fragmentation of the sperm cell.

These pre-selected chemical assays may be any one of Chromomycin A3 (CMA3), Acridine Orange (AO), Sperm Chromatin Structure Assay (SCSA), GoldCyto, sperm chromatin dispersion (SCD) test, and Terminal deoxynucleotidyl transferase dUTP Nick End-Labelling (TUNEL) assay, Toluidine Blue, Aniline Blue and COMET. Here a separate pre-trained neural network is used to approximate the output of each assay type.

Once analysis has been completed, the results are then electronically forwarded. For the purposes of the present example, the results are returned to the laboratory which performed the initial preparation and image capture, but a multitude of approaches and variations would be possible in practice.

Results

This section presents results obtained from preliminary clinical validation studies using the method described above. Here the method was carried out in two independent fertility clinics (one for SCD and one for CMA-3) in parallel with the chemical analysis.

Due to the nature of the SCD test, analysis on a per sperm basis is impossible. The semen sample was imaged prior to the application of the chemical test. This formed the input for the method. The same sample was then assessed after administering the SCD test (GoldCyto was used in this case).

The fragmentation statistics were then recorded for a given patient; reporting number of unfragmented, fragmented and degraded spermatozoa out of a total of 100 counted. The output of the step of approximating the output of the pre-selected chemical assay of sperm DNA fragmentation of the sperm cell was in the form of DNA fragmentation indices (DFIs) for all sperm observed. By thresholding this DFI distribution we are able to provide aggregated statistics akin to those presented by the chemical test.

Contrastingly, the CMA-3 test allows for the same field-of-view to be imaged under brightfield and fluorescence. This enabled one-to-one matching of the brightfield image (and consequently the predicted fragmentation index) to the fluorescence intensity for each individual sperm in every field of view.

Sperm Chromatin Dispersion

Training of the SCD regression model was done on approximately 38 k images (after data augmentation). The data were split into training and validation sets with an 80/20 split point. The neural network achieved an average error of 3.28% and a maximum error of 40.52% when predicting DFI. The SCD neural network was trained on images obtained from the Acridine Orange chemical test (based on SCD). However, the derived network obtains a correlation between 0.15 and 5 0.4 when comparing the network aggregated statistics with the clinical analysis using the GoldCyto chemical test (also based on SCD). Further refinement of the models aim to improve the concordance between the NN predictions and the expert analysis.

Chromomycin A3

The data set was constructed from images captured from 10 patients, totally over 150 k brightfield images of individual spermatozoa (after data augmentation) and corresponding fluorescent images. Table 1 illustrates the performance of the CMA-3 classification network on the validation portion of the dataset.

The regression network obtains a mean error of 6.16% and a maximum error of 31.3% when predicting fluorescent intensity.

TABLE 1

Performance Statistics for Validation Dataset for CMA3 Net.

|  | Precision | Recall | $F_1$-Score | Support |
|---|---|---|---|---|
| Unfragmented | 0.78 | 0.61 | 0.68 | 3402 |
| Fragmented | 0.69 | 0.83 | 0.75 | 3515 |
| Accuracy | — | — | 0.72 | 6917 |
| Macro average | 0.73 | 0.72 | 0.72 | 6917 |
| Weighted average | 0.73 | 0.72 | 0.72 | 6917 |

CONCLUSION

The proposed methodology of digital analysis for the prediction of DNA fragmentation of human sperm images captured using non-destructive preparation offers several points of novelty and unexpected findings:
1. The mimicking of multiple chemical tests using neural networks.
2. Robustness of the neural networks to various input images, degree of blur, focus level, etc.
3. Ensemble approaches, combination of multiple inference techniques, collated together to optimise classification performance.
4. Validation of methodology within a clinical setting.
5. Illustrative use case of sperm selection at the point of ICSI/IVF.

In use, the method of the present invention allows for chemical-free, non-destructive analysis of sperm requiring minimal preparation.

The method of the invention is amenable to the processing of mobile and immobilised spermatozoa.

In both cases the spermatozoa may be alive or dead. In the case of live samples, the technique can be applied to select the best quality sperm (based on DNA fragmentation) to assist with sperm selection for in-vitro fertilisation (IVF) or Intracytoplasmic Sperm Injection (ICSI).

In this regard, it will be appreciated that the method of the present invention affords a number of significant and surprising solutions to address the shortcomings of the prior art, as detailed herein above in the body of the patent specification.

The description is presented by way of example only in the cause of providing what is believed to be the most useful and readily understood description of the principles and conceptual aspects of the invention. In this regard, no attempt is made to show structural details of the invention and/or the equipment utilized therein in more detail than is necessary for a fundamental understanding of the invention.

The invention claimed is:

1. A method for analysing DNA fragmentation in a sperm cell by approximating the output of a pre-selected chemical assay of sperm DNA fragmentation, the method comprising:
   (i) providing an image of the sperm cell, under brightfield and/or phase contrast with a total magnification of 400× to 1000×;
   (ii) evaluating the image of the sperm cell to identify and/or measure a pre-selected biomarker, comprising:
      processing the image of the sperm cell using an image processing neural network to generate a network output that characterizes one or more morphological features of the sperm cell,
      wherein the image processing neural network comprises a plurality of convolutional neural network layers, and
      wherein the pre-selected biomarker is based on the morphological features of the sperm cell; and
   (iii) approximating the output of the pre-selected chemical assay of sperm DNA fragmentation of the sperm cell by subjecting the identified and/or measured biomarker to a first machine learning analysis, comprising:
      processing a model input comprising the identified and/or measured biomarker using an assay prediction machine learning model and in accordance with trained values of a set of machine learning model parameters to generate a prediction for the output of the pre-selected chemical assay of sperm DNA fragmentation of the sperm cell,
      wherein the assay prediction machine learning model generates a model output that comprises a respective prediction for the output of each of a plurality of pre-selected chemical assays of sperm DNA fragmentation of the sperm cell.

2. The method of claim 1, wherein the step of providing an image further comprises:
   (i) providing an image of a plurality of sperm cells; and
   (ii) isolating the image of the sperm cell from the image of a plurality of sperm cells.

3. The method of claim 1, wherein the step of isolating an image of the sperm cell is carried out using a second machine learning analysis.

4. The method of claim 3, wherein the second machine learning analysis is carried out using a second pre-trained neural network.

5. The method of claim 1, wherein the sperm cell is a live sperm cell.

6. The method of claim 1, wherein the image of the sperm cell is from a video of the sperm cell.

7. The method of claim 1, wherein the image of the sperm cell is a microscope image.

8. The method of claim 1, further comprising selecting the sperm cell for use in in-vitro fertilization (IVF) or intracytoplasmic sperm injection (ICSI) based on the approximation of the output of the pre-selected chemical assay of sperm DNA fragmentation.

9. The method of claim 1, wherein the one or more morphological features of the sperm cell comprise one or more of: area of the sperm cell, perimeter of the sperm cell, width of the sperm cell, length of the sperm cell, eccentricity of the sperm cell, ellipticity of the sperm cell, roughness of the sperm cell, elongation of the sperm cell, or regularity of the sperm cell.

10. The method of claim 1, wherein the plurality of pre-selected chemical assays of sperm DNA fragmentation comprises two or more of: Chromomycin A3 (CMA3), Acridine Orange (AO), Sperm Chromatin Structure Assay (SCSA), GoldCyto, sperm chromatin dispersion (SCD) test, Terminal deoxynucleotidyl transferase dUTP Nick End-Labelling (TUNEL) assay, Toluidine Blue, Aniline Blue or Single Cell Gel Electrophoresis (COMET) assay.

11. The method of claim 1, the assay prediction machine learning model is a neural network that comprises:
   a core neural network that is configured to process the model input comprising the identified and/or measured biomarker to generate an embedding of the identified and/or measured biomarker; and
   a plurality of output layers, wherein each output layer is configured to process the embedding of the identified and/or measured biomarker to generate a prediction for an output of a corresponding chemical assay of sperm DNA fragmentation,
   wherein each of the plurality of output layers corresponds to a respective chemical assay of sperm DNA fragmentation which is different from each other output layer.

12. The method of claim 1, further comprising generating a predicted sperm viability score as a combination of the predictions for the outputs of the plurality of pre-selected chemical assays of sperm DNA fragmentation of the sperm cell.

13. The method of claim 1, wherein generating a predicted sperm viability score as a combination of the predictions for the outputs of the plurality of pre-selected chemical assays of sperm DNA fragmentation of the sperm cell comprises:
   processing a model input that comprises the predictions for the outputs of the plurality of pre-selected chemical assays of sperm DNA fragmentation of the sperm cell using a viability prediction machine learning model to generate the predicted sperm viability score.

14. The method of claim 13, wherein the model input processed by the viability prediction machine learning model further comprises the identified and/or measured biomarker.

15. The method of claim 14, wherein providing the image of the sperm cell comprises:
obtaining the image of the sperm cell; and
processing the image of the sperm cell using a super-resolution computational model to update the image of the sperm cell to approximate an image captured at a higher resolution.

16. The method according to claim 15, wherein the super-resolution computational model comprises a bilinear interpolation model.

17. A system comprising:
one or more computers; and
one or more storage devices communicatively coupled to the one or more computers, wherein the one or more storage devices store instructions that, when executed by the one or more computers, cause the one or more computers to perform operations for analysing DNA fragmentation in a sperm cell by approximating the output of a pre-selected chemical assay of sperm DNA fragmentation, the operations comprising:
(i) providing an image of the sperm cell, under brightfield and/or phase contrast with a total magnification of 400× to 1000×;
(ii) evaluating the image of the sperm cell to identify and/or measure a pre-selected biomarker, comprising:
processing the image of the sperm cell using an image processing neural network to generate a network output that characterizes one or more morphological features of the sperm cell,
wherein the image processing neural network comprises a plurality of convolutional neural network layers, and
wherein the pre-selected biomarker is based on the morphological features of the sperm cell; and
(iii) approximating the output of the pre-selected chemical assay of sperm DNA fragmentation of the sperm cell by subjecting the identified and/or measured biomarker to a first machine learning analysis, comprising:
processing a model input comprising the identified and/or measured biomarker using an assay prediction machine learning model and in accordance with trained values of a set of machine learning model parameters to generate a prediction for the output of the pre-selected chemical assay of sperm DNA fragmentation of the sperm cell,
wherein the assay prediction machine learning model generates a model output that comprises a respective prediction for the output of each of a plurality of pre-selected chemical assays of sperm DNA fragmentation of the sperm cell.

18. One or more non-transitory computer storage media storing instructions that when executed by one or more computers cause the one or more computers to perform operations for analysing DNA fragmentation in a sperm cell by approximating the output of a pre-selected chemical assay of sperm DNA fragmentation, the operations comprising:
(i) providing an image of the sperm cell, under brightfield and/or phase contrast with a total magnification of 400× to 1000×;
(ii) evaluating the image of the sperm cell to identify and/or measure a pre-selected biomarker, comprising:
processing the image of the sperm cell using an image processing neural network to generate a network output that characterizes one or more morphological features of the sperm cell,
wherein the image processing neural network comprises a plurality of convolutional neural network layers, and
wherein the pre-selected biomarker is based on the morphological features of the sperm cell; and
(iii) approximating the output of the pre-selected chemical assay of sperm DNA fragmentation of the sperm cell by subjecting the identified and/or measured biomarker to a first machine learning analysis, comprising:
processing a model input comprising the identified and/or measured biomarker using an assay prediction machine learning model and in accordance with trained values of a set of machine learning model parameters to generate a prediction for the output of the pre-selected chemical assay of sperm DNA fragmentation of the sperm cell,
wherein the assay prediction machine learning model generates a model output that comprises a respective prediction for the output of each of a plurality of pre-selected chemical assays of sperm DNA fragmentation of the sperm cell.

* * * * *